(12) United States Patent
Van Ogtrop et al.

(10) Patent No.: US 9,096,564 B2
(45) Date of Patent: Aug. 4, 2015

(54) PROCESSES FOR THE PRODUCTION OF ETHYLENE GLYCOL

(75) Inventors: Jan Van Ogtrop, Amsterdam (NL); Abraham Adriaan Smaardijk, Amsterdam (NL); Jacqueline Hessing, legal representative, Castricum (NL); Hendrik Stichter, Amsterdam (NL)

(73) Assignee: Shell Oil Company, Houston, TX (US)

( * ) Notice: Subject to any disclaimer, the term of this patent is extended or adjusted under 35 U.S.C. 154(b) by 300 days.

(21) Appl. No.: 13/362,835

(22) Filed: Jan. 31, 2012

(65) Prior Publication Data

US 2012/0197048 A1    Aug. 2, 2012

(30) Foreign Application Priority Data

Jan. 31, 2011 (EP) ................................ 11152780

(51) Int. Cl.

| | |
|---|---|
| *C07C 29/09* | (2006.01) |
| *C07D 301/22* | (2006.01) |
| *C07C 29/12* | (2006.01) |
| *C07D 301/04* | (2006.01) |
| *C07C 29/10* | (2006.01) |

(52) U.S. Cl.
CPC ............ *C07D 301/22* (2013.01); *C07C 29/106* (2013.01); *C07C 29/12* (2013.01); *C07D 301/04* (2013.01)

(58) Field of Classification Search
CPC ...................................................... C07C 29/09
USPC ......................................................... 568/858
See application file for complete search history.

(56) References Cited

U.S. PATENT DOCUMENTS

| 4,349,417 A | 9/1982 | Rebsdat et al. | |
| 4,822,926 A | 4/1989 | Dye ............................. | 568/867 |
| 5,336,791 A | 8/1994 | Jennings et al. ............... | 549/538 |
| 6,080,897 A | 6/2000 | Kawabe ........................ | 568/858 |
| 6,184,423 B1 | 2/2001 | Jen | |
| 6,187,972 B1 | 2/2001 | Kawabe et al. ............... | 568/858 |
| 6,437,199 B1 | 8/2002 | Oka et al. | |

FOREIGN PATENT DOCUMENTS

| CN | 1721385 | | 1/2006 | |
| WO | 2004056453 | | 7/2004 | |
| WO | WO-2008009013 | * | 7/2008 | |
| WO | WO2008090138 | | 7/2008 | ........... C07D 301/10 |

OTHER PUBLICATIONS

"Ethylene Oxide", Ullmann's Encyclopedia of Industrial Chemistry, 5th Rev. Ed., vol. A 10, pp. 117-139 (1987).
IPO Search Report dated Apr. 9, 2013 for Ref. TS1658 TAI, ROC (Taiwan) Patent Application No. 097102401.

* cited by examiner

*Primary Examiner* — Yong Chu
*Assistant Examiner* — Sonya Wright

(57) ABSTRACT

A process for the production of ethylene glycol comprising:
(i) supplying ethylene and oxygen and an organic chloride moderator to an EO reactor, thereby producing a reactor product stream;
(ii) supplying the reactor product stream to an EO absorber, thereby producing a fat absorbent stream;
(iii) supplying the fat absorbent stream to an EO stripper, thereby producing a concentrated ethylene oxide stream and a lean absorbent stream;
(iv) recirculating the lean absorbent stream to the EO absorber; and
(v) supplying the ethylene oxide stream and/or the ethylene carbonate stream to hydrolysis reactors with an alkali metal salt hydrolysis catalyst to form an ethylene glycol stream;

wherein the process additionally comprises:
(vi) removing a glycol bleed stream from the ethylene oxide stripper; and
(vii) adding a base to the ethylene oxide stripper such that the pH in the bottom section of the stripper is maintained from 9.5 to 12.0.

8 Claims, 2 Drawing Sheets

PROCESSES FOR THE PRODUCTION OF ETHYLENE GLYCOL

This patent application claims the benefit of EP11152780.0 filed Jan. 31, 2011, which is incorporated herein by reference.

FIELD OF THE INVENTION

The present invention relates to a process for the production of ethylene glycol.

BACKGROUND OF THE INVENTION

Monoethylene glycol is used as a raw material in the manufacture of polyester fibres, polyethylene terephthalate (PET) plastics and resins. It is also incorporated into automobile antifreeze liquids. Monoethylene glycol is typically prepared from ethylene oxide, which is in turn prepared from ethylene. Ethylene and oxygen are passed over a silver oxide catalyst, typically in the presence of an organic chloride moderator, producing a product stream comprising ethylene oxide, carbon dioxide, ethylene, oxygen and water.

The product stream from the ethylene oxide reactor, which may also contain by-products such as organic chlorides, is then supplied to an ethylene oxide absorber. Typically, the ethylene oxide absorber has an initial quench section such as those described in U.S. Pat. No. 4,822,926 A and U.S. Pat. No. 5,336,791 A.

After the quench section, the product stream passes to the main section of the ethylene oxide absorber in which the ethylene oxide is contacted with and absorbed into a lean absorbent stream, which usually comprises water. The resultant aqueous ethylene oxide stream is referred to as 'fat absorbent' and is supplied to an ethylene oxide stripper, wherein ethylene oxide is removed as a concentrated aqueous ethylene oxide stream.

The ethylene oxide obtained from the ethylene oxide stripper may be undergo hydrolysis with water in order to provide monoethylene glycol and also higher glycols such as diethylene glycol and triethylene glycol. Preferably, the hydrolysis occurs in the presence of a hydrolysis catalyst in order to improve the selectivity to monoethylene glycol. Alternatively, the ethylene oxide may be reacted with carbon dioxide in the presence of a carboxylation catalyst to provide ethylene carbonate, and the ethylene carbonate may be reacted with water in the presence of a hydrolysis catalyst to provide ethylene glycol. Such processes are described in U.S. Pat. No. 6,080,897 A and U.S. Pat. No. 6,187,972 B1 and provide high selectivity to monoethylene glycol.

Homogeneous catalysts that are commonly used to promote hydrolysis of ethylene oxide or ethylene carbonate to ethylene glycol include basic alkali metal salts such as potassium carbonate, potassium hydroxide and potassium bicarbonate. The present inventors have found that during the operation of a process for preparing ethylene glycol, such hydrolysis catalysts can become deactivated during operation and that at least part of the deactivation occurs when chloroethanol, formed from the reaction of ethylene oxide with chlorides present in the EO reactor, reacts with the hydrolysis catalyst to form inorganic chlorides (such as KCl), which are inactive as hydrolysis catalysts, and ethylene glycol.

This deactivation means that it is necessary to provide additional fresh catalyst during operation. Further, a catalyst bleed stream must be employed in order to remove the deactivated catalyst, as well as other decomposition products from the process.

The present inventors have, therefore, sought to provide an improved process wherein the amount of chloroethanol present in the process is reduced and also wherein the decomposition of the hydrolysis catalyst is decreased or avoided.

SUMMARY OF THE INVENTION

Accordingly, the present invention provides a process for the production of ethylene glycol comprising the steps of:

(i) supplying ethylene and oxygen and an organic chloride moderator to an ethylene oxide reactor wherein ethylene and oxygen react in the presence of a catalyst to produce ethylene oxide, thereby producing a reactor product stream;

(ii) supplying the reactor product stream to an ethylene oxide absorber wherein ethylene oxide is recovered from the reactor product stream by absorption in water in the absorber section, thereby producing a fat absorbent stream;

(iii) supplying the fat absorbent stream to an ethylene oxide stripper wherein the fat absorbent stream is steam stripped, thereby producing a concentrated ethylene oxide stream and a lean absorbent stream;

(iv) recirculating the lean absorbent stream to the ethylene oxide absorber;

(v) optionally supplying the concentrated ethylene oxide stream to one or more carboxylation reactors wherein ethylene oxide reacts with carbon dioxide to form an ethylene carbonate stream; and (vi) supplying the concentrated ethylene oxide stream and/or the ethylene carbonate stream to one or more hydrolysis reactors wherein ethylene oxide and/or ethylene carbonate reacts with water in the presence of a hydrolysis catalyst selected from one or more basic alkali metal salts to form an ethylene glycol stream;

wherein the process comprises the additional steps of:

(vii) removing a glycol bleed stream from the ethylene oxide stripper; and (viii) adding a base to the ethylene oxide stripper such that the pH in the bottom section of the stripper is maintained in the range of from at least 9.5 to at most 12.0.

DETAILED DESCRIPTION OF THE INVENTION

Figure 1:
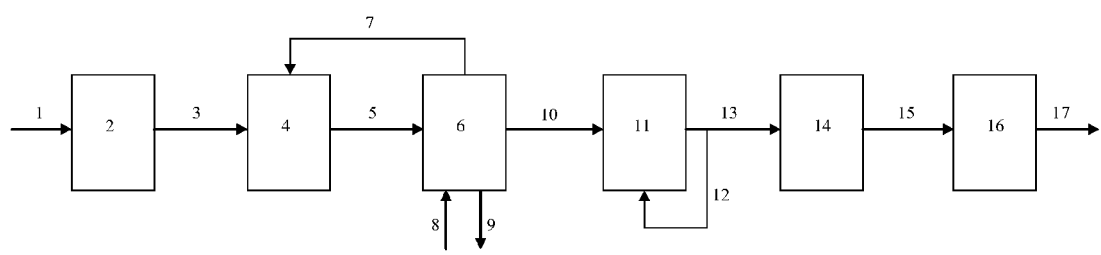
FIG. 1 is a schematic diagram showing a preferred embodiment of the process according to the invention for producing ethylene glycol.

The present inventors have surprisingly found that, in a process for the production of ethylene oxide from ethylene comprising a catalytic hydrolysis step, the presence of chloroethanol in the process and the decomposition and deactivation of the hydrolysis catalyst can be reduced if the pH in the bottom section of the stripper used to extract ethylene oxide from an aqueous absorbent is maintained in the range of from 9.5 to 12.0. This can be achieved by the addition of a base to the stripper.

The reaction of ethylene and oxygen to produce ethylene oxide in an ethylene oxide reactor is well known to the skilled person. The oxygen may be supplied as oxygen or as air, but is preferably supplied as oxygen. Ballast gas, for example methane, is typically supplied to allow operation at high oxygen levels without causing a flammable mixture.

The organic chloride moderator is supplied for catalyst performance control. Preferred organic chloride moderators are chlorohydrocarbons. More preferably, the organic chloride moderator is selected from the group of methyl chloride, ethyl chloride, ethylene dichloride, vinyl chloride, and mixtures thereof. The most preferred organic chloride moderators are ethyl chloride and ethylene dichloride.

The ethylene, oxygen, ballast gas and organic chloride moderator are preferably supplied to recycle gas that is supplied to the ethylene oxide reactor from the ethylene oxide absorber.

The ethylene oxide reactor is suitably a multitubular, fixed bed reactor. The catalyst is preferably finely dispersed silver and optionally promoter metals on a support material, for example, alumina. The reaction is preferably carried out at pressures of greater than 10 bar and less than 30 bar and temperatures of greater than 200° C. and less than 300° C.

Most of the ethylene reacts to form ethylene oxide, but a portion of the ethylene will be oxidised fully, providing carbon dioxide and water.

The reactor product stream is supplied to the quench section of an ethylene oxide absorber. After the quench section, the product stream passes to the main section of the ethylene oxide absorber in which the ethylene oxide is contacted with and absorbed into a lean absorbent stream, which usually comprises water. The resultant aqueous ethylene oxide stream is referred to as 'fat absorbent' and is supplied to an ethylene oxide stripper, wherein ethylene oxide is removed as a concentrated aqueous ethylene oxide stream.

Preferably, overhead vapours from the ethylene oxide absorber are recycled to the ethylene oxide reactor. A portion of this recycle gas is preferably diverted through an absorber for carbon dioxide removal and is then returned to the recycle stream. A vent stream is typically taken from the recycle gas to reduce the build-up of inerts such as ethane, argon and nitrogen and to remove impurities.

The aqueous stream exiting the ethylene oxide absorber, the fat absorbent stream, is supplied to an ethylene oxide stripper. In a typical ethylene oxide stripper, a concentrated ethylene oxide stream leaves the top of the stripper and a lean absorbent stream leaves the bottom of the stripper. The lean absorbent stream is recirculated to the ethylene oxide absorber and is preferably cooled before it is supplied to the ethylene oxide absorber.

A glycol bleed stream is removed from the stripper. This stream comprises glycols formed from the reaction of the ethylene oxide with water and is removed to prevent build up of glycols at this stage in the process. MEG may be separated from this stream and purified with the rest of the MEG produced in the overall process. The glycol bleed stream may also contain heavy glycols and salts.

The concentrated aqueous ethylene oxide stream is then supplied to the ethylene oxide to ethylene glycol section of the process, which comprises a catalytic hydrolysis step.

In a preferred embodiment of the present invention, in which the ethylene oxide is transformed to ethylene carbonate before the hydrolysis step, the aqueous ethylene oxide stream is provided to one or more carboxylation reactors. Carbon dioxide and a catalyst stream are also supplied.

The catalyst stream comprises one or more catalysts that promote carboxylation and, optionally, hydrolysis. In a preferred embodiment of the present invention, the catalyst stream comprises one or more catalysts that promote carboxylation and hydrolysis. In this embodiment, if only one catalyst is present, then the catalyst must promote carboxylation and hydrolysis. If two or more catalysts are present, then each catalyst can promote carboxylation or hydrolysis or can promote both reactions (provided that at least one catalyst promotes carboxylation and at least one catalyst promotes hydrolysis).

In the present invention, preferably the one or more catalysts that promote carboxylation and, optionally, hydrolysis is/are homogeneous. Homogeneous catalysts that are known to promote carboxylation include alkali metal halides such as potassium iodide and potassium bromide, and halogenated organic phosphonium or ammonium salts such as tributylmethylphosphonium iodide, tetrabutylphosphonium iodide, triphenylmethylphosphonium iodide, triphenyl-propylphosphonium bromide, triphenylbenzylphosphonium chloride, tetraethylammonium bromide, tetramethylammonium bromide, benzyltriethylammonium bromide, tetrabutylammonium bromide and tributylmethylammonium iodide. Homogeneous catalysts that are known to promote hydrolysis include basic alkali metal salts such as potassium carbonate, potassium hydroxide and potassium bicarbonate, or alkali metal metalates such as potassium molybdate. Preferred homogeneous catalyst systems include a combination of potassium iodide and potassium carbonate, and a combination of tributylmethylphosphonium iodide and potassium carbonate.

Alternatively, a heterogeneous catalyst system may be used. Such a catalyst system would suitably comprise ions such as halides, hydroxide or carbonates immobilised on a solid support such as an ion exchange resin.

Carboxylation of the aqueous ethylene oxide stream in the presence of carbon dioxide to produce a stream comprising the corresponding ethylene carbonate occurs in one or more carboxylation reactors. If more than one reactor is present, they are preferably arranged in series.

The carboxylation reactors are suitably two-phase flow reactors operating at a pressure in the range of from 0.8 to 3.0 MPa and a temperature in the range of from 50 to 180° C.

The carboxylation reactors will preferably each be provided with a liquid recycle, wherein liquid is removed from the reactor and then recycled to the bottom of the reactor. The recycle stream can be heated or cooled in order to provide improved temperature control to the carboxylation reactor.

Step (vi) of the process of the present invention comprises supplying either the aqueous ethylene oxide stream from the stripper or the stream comprising ethylene carbonate to one or more hydrolysis reactors, wherein the ethylene oxide and/or ethylene carbonate present react with water in the presence of a catalyst to form an aqueous ethylene glycol stream.

If required, a hydrolysis catalyst stream is supplied to the one or more hydrolysis reactors. Such a stream may be required if the aqueous ethylene oxide stream was supplied to the hydrolysis reactors without first undergoing the optional carboxylation reaction of step (v). Alternatively, the hydrolysis catalyst may be required if the catalyst stream supplied to the carboxylation reactors did not contain a catalyst that promoted hydrolysis to a sufficient extent or if, for any reason, not enough hydrolysis catalyst is present in the stream supplied to the one or more hydrolysis reactors.

In the present invention, the hydrolysis catalyst is suitably homogeneous. Homogeneous catalysts that are known to promote hydrolysis include basic alkali metal salts such as potassium carbonate, potassium hydroxide and potassium bicarbonate, or alkali metal metalates such as potassium molybdate. In the present process, preferred homogeneous catalysts that are known to promote hydrolysis include basic alkali metal salts such as potassium carbonate, potassium hydroxide and potassium bicarbonate.

The one or more hydrolysis reactors may be any suitable reactor type. Preferably, the hydrolysis reactors are baffled reactors. If there is more than one hydrolysis reactor it is preferred that the hydrolysis reactors are connected in series.

In one embodiment of the invention, at least one of the one or more hydrolysis reactors is a baffled reactor, wherein the baffled reactor has at least 3, preferably at least 4 compartments, the compartments are formed by internal baffles and the internal baffles provide a sinuous route for reaction fluid through the reactor.

Optionally, steam is injected into the baffled reactor.

The temperature in the one or more hydrolysis reactors is typically from 100 to 200° C., preferably from 100 to 180° C. The pressure in the one or more hydrolysis reactors is typically from 0.1 to 3 MPa.

The ethylene glycol product stream emerging from the one or more hydrolysis reactors is then supplied to a dehydration and purification section in order to remove water and to produce the desired MEG.

The base that is added in step (vii) of the invention is preferably an aqueous alkaline solution, for example, an aqueous sodium hydroxide or potassium hydroxide solution. The concentration of the aqueous alkaline solution is preferably at least 5 wt %, more preferably at least 10 wt %. Preferably it is at most 50 wt %, more preferably at most 30 wt %.

The aqueous alkaline solution is a liquid and is added to liquids (i.e. it is not added to reactants or products in the gaseous phase).

The base is added to the ethylene oxide stripper such that the pH in the bottom section of the stripper is maintained in the range of from at least 9.5 to at most 12.0. Preferably, the pH in the bottom section of the stripper is maintained at more than 9.5. Also preferably, the pH is at most 10.5.

As used herein, the term 'bottom section of the stripper' refers to the downstream portion of the stripper. Suitable locations for measurement of the pH within the bottom section of the stripper include in the stripper itself, in the lean absorbent stream which is removed from the bottom of the stripper or in the glycol bleed stream.

The pH may be monitored by sampling at regular intervals or by continuous online monitoring.

FIG. 1 is a schematic diagram showing a preferred embodiment of the process according to the present invention. One or more feeds containing ethylene and oxygen (1) are supplied to an ethylene oxide reactor (2). The reactor product stream (3) from the ethylene oxide reactor (2) is then fed to an absorber (4) where it is contacted with lean absorbent (7). The fat absorbent stream (5) is provided to an ethylene oxide stripper (6), wherein the ethylene oxide is separated and the lean absorbent (7) is recycled to the absorber (4). The stripper has a glycol bleed stream (9) and base (8) is added to the stripper (6) in order to maintain the pH of the glycol bleed stream (9) in the range of from at least 9.5 to at most 12.0. In this embodiment the concentrated ethylene oxide stream (10) from the stripper (6) is supplied to one or more carboxylation reactors (11), each of which has a liquid recycle (12). The stream comprising ethylene carbonate (13) produced in the one or more carboxylation reactors (11) is supplied to one or more hydrolysis reactors (14) wherein hydrolysis occurs in the presence of a hydrolysis catalyst. The resultant ethylene glycol stream is then subjected to dehydration and purification in the dehydration and purification section (16) of the process in order to produce purified ethylene glycols (17).

Figure 2:
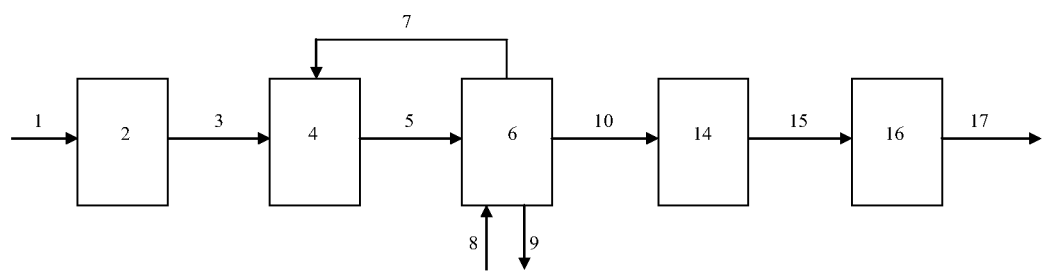
FIG. 2 is a schematic diagram showing a preferred embodiment of the process according to the invention for producing ethylene glycol.

FIG. 2 is a schematic diagram showing a preferred embodiment of the process according to the present invention. In this embodiment the concentrated ethylene oxide stream (10) from the stripper (6) is supplied to one or more hydrolysis reactors (14) wherein hydrolysis occurs in the presence of a hydrolysis catalyst.

It will be clear to the skilled person, that as schematic diagrams these figures do not show all necessary inputs and recycle streams that may be present in the process.

What is claimed is:

1. A process for the production of ethylene glycol comprising the steps of:
    (i) supplying ethylene and oxygen and an organic chloride moderator to an ethylene oxide reactor wherein ethylene and oxygen react in the presence of a catalyst to produce ethylene oxide, thereby producing a reactor product stream;
    (ii) supplying the reactor product stream to an ethylene oxide absorber comprising an absorber section, wherein ethylene oxide is recovered from the reactor product stream by absorption in water in the absorber section, thereby producing a fat absorbent stream;
    (iii) supplying the fat absorbent stream to an ethylene oxide stripper wherein the fat absorbent stream is steam stripped, thereby producing a concentrated ethylene oxide stream and a lean absorbent stream;
    (iv) recirculating the lean absorbent stream to the ethylene oxide absorber;
    (v) optionally supplying the concentrated ethylene oxide stream to one or more carboxylation reactors wherein ethylene oxide reacts with carbon dioxide to form an ethylene carbonate stream; and
    (vi) supplying the concentrated ethylene oxide stream and/or the ethylene carbonate stream to one or more hydrolysis reactors wherein ethylene oxide and/or ethylene carbonate reacts with water in the presence of a hydrolysis catalyst selected from one or more basic alkali metal salts to form an ethylene glycol stream;
    wherein the process comprises the additional steps of:
    (vii) removing a glycol bleed stream from the ethylene oxide stripper; and
    (viii) adding a base to the ethylene oxide stripper such that the pH in the bottom section of the stripper is maintained at more than 9.5 to at most 12.0.

2. A process according to claim 1, wherein the concentrated ethylene oxide stream is supplied to one or more carboxylation reactors wherein ethylene oxide reacts with carbon dioxide to form an ethylene carbonate stream in step (v).

3. A process according to claim 1, wherein the hydrolysis catalyst is selected from potassium carbonate, potassium hydroxide and potassium bicarbonate.

4. A process according to claim 3, wherein the pH is measured in the glycol bleed stream.

5. A process according to claim 1, wherein the base is selected from the group consisting of potassium hydroxide and sodium hydroxide.

6. A process according to claim 1, wherein the pH is at most 10.5.

7. A process according to claim 1, wherein the organic chloride moderator is a chlorohydrocarbon.

8. A process according to claim 1, wherein the organic chloride moderator is selected from the group consisting of methyl chloride, ethyl chloride, ethylene dichloride, vinyl chloride, and mixtures thereof.

* * * * *